United States Patent [19]

Wannag

[11] 4,044,771

[45] Aug. 30, 1977

[54] FORCEPS MADE IN ONE PIECE

[76] Inventor: Arne T. Wannag, 11 A Palnasvagen, 133 00 Saltsjobaden, Sweden

[21] Appl. No.: 645,602

[22] Filed: Dec. 31, 1975

[51] Int. Cl.² ............................................. A61B 17/30
[52] U.S. Cl. ....................................... 128/354; 81/43
[58] Field of Search ..................... 128/321, 354; 81/43

[56] References Cited

U.S. PATENT DOCUMENTS

| | | | |
|---|---|---|---|
| 2,685,880 | 8/1954 | Curutchet | 81/43 X |
| 3,140,715 | 7/1964 | Whitton et al. | 128/354 X |
| 3,265,068 | 8/1966 | Holohan | 128/321 |
| 3,653,389 | 4/1972 | Shannon | 128/354 |

Primary Examiner—Channing L. Pace
Attorney, Agent, or Firm—Ulle C. Linton

[57] ABSTRACT

A forceps made in one piece of a plastic material has two arms having each a flat tip of a rectangular or square configuration. Said tips face each other and the arms are of a rigid beam-shaped structure but join in flexible portions. Near to the transition between said beam-shaped structure and said flexible portion each arm has a projection and said projections are dimensioned to engage each other when said tips are pressed against each other surface to surface.

3 Claims, 5 Drawing Figures

FORCEPS MADE IN ONE PIECE

This invention relates to a pair of forceps made in one piece, preferably by injection moulding of a plastic material.

Especially in the medical attendance there is a pronounced need for effective and cheap forceps preferably of the disposable type.

Such a pair of forceps should be designed such that the arms of the forceps will have a lateral stability in relation to each other, that a high pressure against the suture or similar to be secured may be achieved and that cotton wool and similar will not tend to cling to the tips thereof.

However, none of the hitherto produced forceps made from plastic materials have been able to simultaneously fulfill all these claims and thus, the object of the invention is to provide a pair of forceps that in contrast to the previously known structures do fulfill all the claims placed upon a useful pair of forceps.

To accomplish these and other objects the invention has the characteristics disclosed in the following claims.

An examplifying embodiment of the invention is shown in the drawings, wherein

Figure 4:
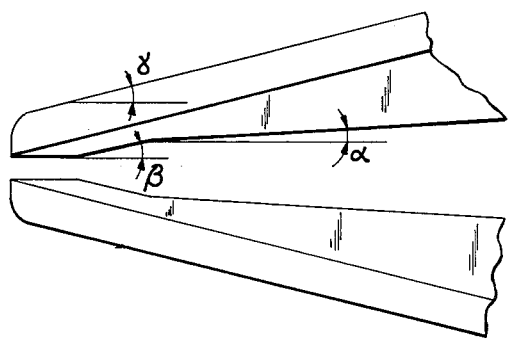
FIG. 4 shows on a larger scale the actual tips of the forceps and shows the flat active surface, thereof
Figure 5:
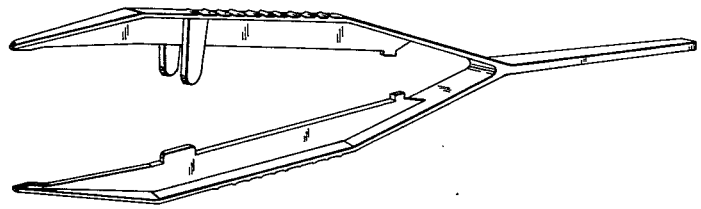
FIG. 5 shows the improved forceps in a perspective view.

The improved pair of forceps preferably have a flat handle portion 1 and arms 2a and 2b of the forceps extend therefrom. The arms comprise rather flexible portions 3a, 3b of rectangular section in the parts thereof joining the handle portion but the rest of the extension of the arms of the forceps are beams of T-shaped section. Thus, according to the invention the arms of the forceps should with the exception of portions 3a, 3b be as rigid to bending as possible. The web portion 5 should be relatively high at point 4a, 4b, for a reason to be explained. The height of the web portion thereafter successively increases towards zone 6, wherein compression of the forceps usually occurs. Preferably, through this zone the height of the beam is constant and thereafter successively decreases in an outward direction towards the tips 7a, 7b of the arms of the forceps. As may be clearly seen in FIG. 4 the height of the beam linearly decreases following an angle $\alpha$ to a point 8 at a distance from the tips of the forceps. From point 8 the height of the beam only slightly decreases since angle $\beta$ substantially corresponds to the angle $\gamma$, which the outer portion of the arm of the forceps defines with the horizontal reference plan, used in the drawing. It is understood that hereby the arms will have two flat and rectangular surfaces 10a, 10b facing each other. These surfaces are of decisive importance to the function of the forceps and it may be mentioned that the size of the surfaces in a practical embodiment approximately amount to 2 mm × 2 mm.

Figure 1:
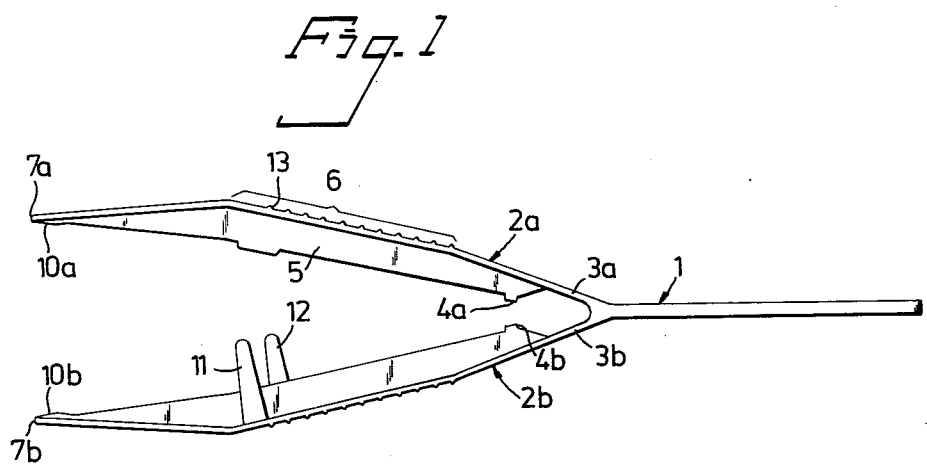
FIG. 1 is a side view of the forceps in the normal position with the arms open in relation to each other.
Figure 2:
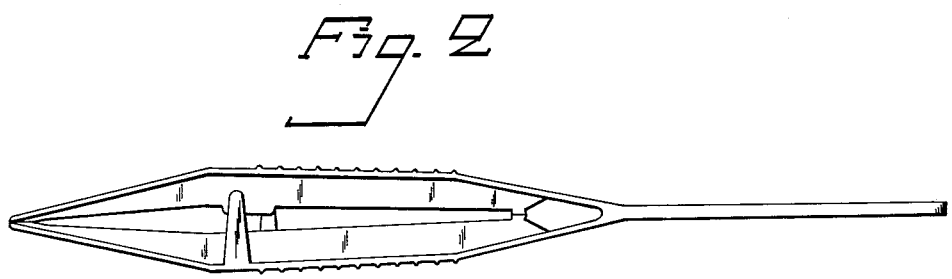
FIG. 2 is a similar side view of the forceps in the operative position thereof, in which the tips of the forceps engage each other and the suture, etc. to be secured.
Figure 3:
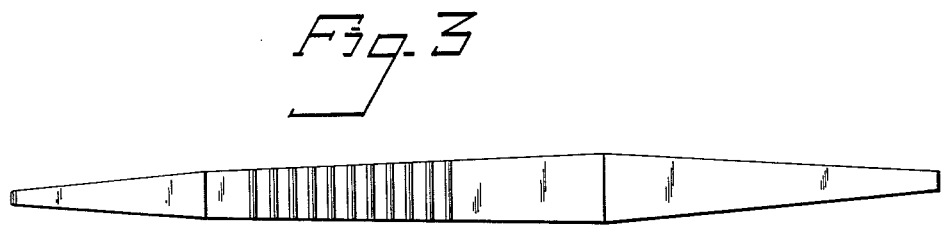
FIG. 3 shows the forceps, in a plan view.

In order to guide the arms of the forceps in lateral relation to each other one of the arms 2b has a projection 11 extending from the front side thereof and a projection 12 extending from the rear side thereof. In order to make these projections able to be made in a simple injection moulding tool without movable jaws, said projections 11 and 12 are displaced in relation to each other seen in the longitudinal direction of the arm. It is obvious that by pressing the arms together the projections will guide the web portion of the arm 2a between themselves, as may be seen in FIG. 2.

In a manner known per se, the portions of the arms, which in use of the forceps are acted upon by the hands of the user and are positioned within zone 6, preferably are provided with ribs 13 or the like to obtain a relatively slip-safe grip.

The invention is based upon the fact that a pair of forceps for hospital use must be able to perform a very strong retaining force since forceps etc are used to extract sutures and the like. These forceps are often very slightly compressible and thus, when working with relatively coarse and hard sutures, it is not possible to provide for the desired retention by for examle making the tips of the forceps grooved. According to the invention the required retaining force is achieved in giving the arms of the forceps such a shape that by pressing the same against the object they form beams having great bending strength and furthermore providing the tips with suitably rectangular grip surfaces 10a, 10b facing each other.

By selecting the points 4a, 4b so that the arms engage each other in these points almost at the same time as the grip surfaces 10a, 10b are brought to contact each other, it is obtained that the arms may be considered as beams placed upon a support, partly 4a, 4b and partly at 10a, 10b. The elastical deformation of the arms is thereby minimized and by providing the grip surfaces 10a, 10b with an extension of 2 mm or more, at least in the direction towards the handle portion an effective retaining force is obtained on the suture when for instance extraction of sutures is to take place.

It will be understood that the grip surfaces 10a, 10b define a small angle with each other exactly in the moment when they engage each other in such a manner that in the moment of engagement the ends of the surfaces positioned farthest from the handle portion engage each other but the angle is so small that the slight deformation of the beams obtained by a relatively modest manual compression of the arms of the forceps brings the grip surfaces to a totally parallel mutual engaging position.

What I claim is:

1. Forceps of one piece of material preferably a plastic material, comprising a pair of arms being joined together at one end thereof and having tips at their other free ends, said arms having a relatively short distance from their joining point two projections which face each other and are dimensioned to engage each other by abutment substantially when the tips of said arms contact each other, the portion of each of said arms which is located between said projection and said joining point being flexible, the portion of each of said arms between said projection and said tip being relatively rigid and for such purpose are dimensioned for a mnimum deflection when said second portions are supported by the two spaced apart supports, that is said tips and said projections, and in use are to be manually pressed towards each other, said manual pressure acting intermediate said supports, said tips forming planar gripping surfaces facing each other and having a relatively large extension in the length direction as well as in the transverse direction of said arms, said gripping surfaces forming such an angle with the rest of said arms that said gripping surfaces just when said projections engage each other by abutment will be in contact with each other along their entire surface.

2. Forceps as claimed in claim 1, wherein said arms project from a preferably planar handle portion and have a substantially rectangular section between said handle portion and said projections while the rest of said arms have a T-shaped section.

3. Forceps as claimed in clain 1 wherein said arms provide a first and a second arm, said second arm being provided with a pair of guide projections which are spaced apart in the transverse directin of said arm, the distance between said guide projections in the transverse direction of said arm being such that in bringing said arms towards each other said guide projections will guidingly embrace part of said first arm, and said guide projections are spaced in relation to each other also in the longitudinal direction of said arm.

* * * * *